US008962297B2

(12) United States Patent
Seal et al.

(10) Patent No.: US 8,962,297 B2
(45) Date of Patent: Feb. 24, 2015

(54) BACTERIOPHAGE LYTIC ENZYMES AS ALTERNATIVE ANTIMICROBIALS

(75) Inventors: Bruce S. Seal, Athens, GA (US); Gregory R. Siragusa, Waukesha, WI (US); Ibn Mustafa A. Simmons, Athens, GA (US); Johnna K. Garrish, Hull, GA (US); David M. Donovan, Baltimore, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 839 days.

(21) Appl. No.: 12/874,138

(22) Filed: Sep. 1, 2010

(65) Prior Publication Data

US 2012/0052546 A1 Mar. 1, 2012

(51) Int. Cl.
| | |
|---|---|
| *C12N 7/01* | (2006.01) |
| *C12Q 1/68* | (2006.01) |
| *A23B 4/14* | (2006.01) |
| *C12N 9/80* | (2006.01) |
| *A23K 1/165* | (2006.01) |
| *A23K 1/18* | (2006.01) |

(52) U.S. Cl.

CPC ................ *C12N 9/80* (2013.01); *A23K 1/1653* (2013.01); *A23K 1/1826* (2013.01); *C12Y 305/01028* (2013.01); *C12N 2795/10321* (2013.01); *C12N 2795/10322* (2013.01); *C12N 2795/10332* (2013.01)

USPC .......... 435/235.1; 435/5; 536/23.2; 536/23.4; 536/23.7; 426/310; 426/335; 426/532

(58) Field of Classification Search

CPC .................................... A23B 4/10; A23B 7/16

See application file for complete search history.

(56) References Cited

U.S. PATENT DOCUMENTS 7,371,375 B2 * 5/2008 Zimmer et al. .............. 424/94.1

OTHER PUBLICATIONS

Bowie et al (Science, 1990, 247:1306-1310).*
Zimmer et al Appl. Environ. Microbiol. Nov. 2002, 68 (11) pp. 53-11-5317.*
UniProt_201207, Accession number: B6CXF7 (Nov. 25, 2008).*

* cited by examiner

*Primary Examiner* — Padma V Baskar
(74) *Attorney, Agent, or Firm* — Elizabeth R. Sampson; John D. Fado; Lesley Shaw

(57) ABSTRACT

The present invention relates to isolated *Clostridium perfringens* bacteriophage lytic enzymes from baccteriophages CP26F and CP39O, and uses in controlling *Clostridium perfringens.*

17 Claims, 3 Drawing Sheets

MVIIGSRYGHSENCRGAKGLRDEVDAMKPLHFEFKKIMEQYGHTIIDCCSNANTQNGELSEGARKANAQILDLFISWHGNKG
GGQGCEAWIANNSRAKPYAERMCKNFSSLGFKNRGVKYSDKYYEMRNINAPNIIFETLFLDSEKDISIWSPIPYEVMARYLA
NAIDPNIPLEKEQDYYRVCVQRFTNKEDAEKAQQRISNELGYYCFAEKI

FIG. 1

ATGGTGATAATTGGAAGTAGATATGGTCATTCTGAAAATTGCAGAGGGGCTAAAGGATTAAGAGATGAAGTGGACGCT
ATGAAACCTCTTCATTTTGAATTCAAAAAAATAATGGAACAATATGGACATACTATAATTGATTGTTGCTCCAACGCTA
ACACTCAAAACGGAGAGTTGTCAGAAGGTGCAAGGAAAGCAAATGCACAAATTTTGGATTTATTTATATCTTGGCATG
GTAATAAAGGTGGTGGACAAGGTTGTGAAGCTTGGATTGCTAACAATTCAAGAGCTAAGCCTTATGCTGAAAGAATGT
GCAAAAACTTTTCTAGTTTAGGGTTTAAAAaTAGAGGTGTTAAATATAGTGATAAATATTATGAAATGAGAAATATAAA
CGCGCCTAATATAATCTTTGAAACTTTATTTTTAGATAGCGAGAAGGATATTTCCATTTGGTCACCAATCCCATATGAGG
TTATGGCTAGATATTTAGCAAATGCTATCGACCCTAATATACCACTAGAAAAGGAACAAGACTATTATAGAGTTTGTGT
ACAAAGATTCACAAATAAAGAAGATGCTGAAAAAGCGCAACAAAGAATAAGCAATGAGCTAGGTTATTATTGCTTTGC
CGAAAAGATATAG

FIG. 2

MKIALRGGHSPNCKGANVLRDEQSCMWALADEVEKVLTSHGHTVVRCETTLSNEREDVRQGAKKGYNCDMFISLHMNAS
DGRGNGTEAWVARSARSSIKEIASRLCKNYATLGLQNRGVKEKNYWEMTDTNCPNIIFETMFCDDKHDIDIWASTSWDKLA
RLIANAIDPNIPLEKEQDYYRVCVQRFTNKEDAEKAQQRISNELGYYCFAEKI

FIG. 3 atgaaaatagctttaagaggtggacattcacctaattgcaaaggtgctaacgttttaagagatgagcaatcttgcatgtgggctttagctgatgaagtagaaaaagttttaacctctcatggtcataccgtt
gtaagatgtgaaacaactttatcaaatgaaagagaagatgtaagacaaggggctaaaaaaggttataattgcgatatgtttatctctcttcacatgaatgcaagtgacggtcgaggaaatggcacggaa
gcgtgggttgctagaagtgcgagaagttctataaaagaaattgcttcaagattatgcaaaaactatgcaactttaggattgcaaaacagaggtgtaaaagagaagaattactgggaaatgacagatac
aaattgccctaatattattttttgaaactatgttctgtgatgataagcatgatatagatatatgggcttcaacctcttgggataaattagcgagattaatcgcaaatgctatcgaccctaatataccactagaaa
aggaacaagactattatagagtgtgtgtacaaagatttacaaataaagaagatgcagaaaaagcgcaacaaagaataagcaatgagctaggttattattgctttgccgaaaagata<u>tag</u>

FIG. 4

```
39O lysin   1 MK I A L R G GHS P NC K GA NV L RDE Q S C M W A L A D E V E K V LTSH GHTVV R C E T T 50
26F lysin   1 V I I G S R Y GHS E NC R GA K GLRDE V DA M K P L HF E FK K I MEQY GHTIID C S N 50
                I . R  GHS  NC.GA  .LRDE       M   L  E    K.       GHT.. C .

39O lysin  51 L SNER E DV R Q GAKK G - - Y N C D M FI S L H M N A SD G R GN C T EAWV A R SA R SS I 98
26F lysin  51 A NTQN G E L S E GARK A N A Q I L D L FI S W H G N K - - G GQ G C EAWI A NNS R - - A 96
              .        . .   GA.K.NA     D   FIS  H N    SDG  G.G  EAW.A    RSS.

39O lysin  99 K E I A S R L C KNY A TL G L Q NR GV K - EK N Y WE M TDT N C PNIIFET M F C D DK H D 147
26F lysin  97 K PY A E R M C KNF S SL G FK NR GV KY SDK Y Y EM R NI N A PNIIFET L F L D SE K D 146
              K   A   R  CKN. .LG   NRGVKY     Y.EM   N  PNIIFET  F  D   .D 39O lysin 148 I D I W A ST S W DK L A R L IANAIDPNIPLEKEQDYYRVCVQRFTNKEDAEKAQ 197
26F lysin 147 I S I W SPI P Y EV M A R Y LANAIDPNIPLEKEQDYYRVCVQRFTNKEDAEKAQ 196
              I  IW              AR  .ANAIDPNIPLEKEQDYYRVCVQRFTNKEDAEKAQ 39O lysin 198 QRISNELGYYCFAEKI 213
26F lysin 197 QRISNELGYYCFAEKI 212
              QRISNELGYYCFAEKI
```

FIG. 5

SEQUENCE LISTING

```
<160> NUMBER OF SEQ ID NOS: 8

<210> SEQ ID NO 1
<211> LENGTH: 213
<212> TYPE: PRT
<213> ORGANISM: Bacteriophage CP26F

<400> SEQUENCE: 1

Met Val Ile Ile Gly Ser Arg Tyr Gly His Ser Glu Asn Cys Arg Gly
1               5                   10                  15

Ala Lys Gly Leu Arg Asp Glu Val Asp Ala Met Lys Pro Leu His Phe
            20                  25                  30

Glu Phe Lys Lys Ile Met Glu Gln Tyr Gly His Thr Ile Ile Asp Cys
        35                  40                  45

Cys Ser Asn Ala Asn Thr Gln Asn Gly Glu Leu Ser Glu Gly Ala Arg
    50                  55                  60

Lys Ala Asn Ala Gln Ile Leu Asp Leu Phe Ile Ser Trp His Gly Asn
65                  70                  75                  80

Lys Gly Gly Gly Gln Gly Cys Glu Ala Trp Ile Ala Asn Asn Ser Arg
```

85                  90                  95
Ala Lys Pro Tyr Ala Glu Arg Met Cys Lys Asn Phe Ser Ser Leu Gly
                100                 105                 110

Phe Lys Asn Arg Gly Val Lys Tyr Ser Asp Lys Tyr Tyr Glu Met Arg
            115                 120                 125

Asn Ile Asn Ala Pro Asn Ile Ile Phe Glu Thr Leu Phe Leu Asp Ser
        130                 135                 140

Glu Lys Asp Ile Ser Ile Trp Ser Pro Ile Pro Tyr Glu Val Met Ala
145                 150                 155                 160

Arg Tyr Leu Ala Asn Ala Ile Asp Pro Asn Ile Pro Leu Glu Lys Glu
                165                 170                 175

Gln Asp Tyr Tyr Arg Val Cys Val Gln Arg Phe Thr Asn Lys Glu Asp
            180                 185                 190

Ala Glu Lys Ala Gln Gln Arg Ile Ser Asn Glu Leu Gly Tyr Tyr Cys
        195                 200                 205

Phe Ala Glu Lys Ile
    210

<210> SEQ ID NO 2
<211> LENGTH: 642
<212> TYPE: DNA
<213> ORGANISM: Bacteriophage CP26F

<400> SEQUENCE: 2
atggtgataa ttggaagtag atatggtcat tctgaaaatt gcagaggggc taaaggatta      60
agagatgaag tggacgctat gaaacctctt cattttgaat tcaaaaaaat aatggaacaa     120
tatggacata ctataattga ttgttgctcc aacgctaaca ctcaaaacgg agagttgtca     180
gaaggtgcaa ggaaagcaaa tgcacaaatt ttggatttat ttatatcttg catggtaat      240 aaaggtggtg acaaggttg tgaagcttgg attgctaaca attcaagagc taagccttat      300
gctgaaagaa tgtgcaaaaa cttttctagt ttagggttta aaatagagg tgttaaatat      360 agtgataaat attatgaaat gagaaatata aacgcgccta atataatctt tgaaacttta     420
tttttagata gcgagaagga tatttccatt tggtcaccaa tcccatatga ggttatggct     480
agatatttag caaatgctat cgaccctaat ataccactag aaaaggaaca agactattat     540
agagtttgtg tacaaagatt cacaaataaa gaagatgctg aaaaagcgca acaaagaata     600
agcaatgagc taggttatta ttgctttgcc gaaaagatat ag                        642

<210> SEQ ID NO 3
<211> LENGTH: 213
<212> TYPE: PRT
<213> ORGANISM: Bacteriophage CP390

<400> SEQUENCE: 3

Met Lys Ile Ala Leu Arg Gly Gly His Ser Pro Asn Cys Lys Gly Ala
1               5                   10                  15

Asn Val Leu Arg Asp Glu Gln Ser Cys Met Trp Ala Leu Ala Asp Glu
            20                  25                  30

Val Glu Lys Val Leu Thr Ser His Gly His Thr Val Val Arg Cys Glu
        35                  40                  45

Thr Thr Leu Ser Asn Glu Arg Glu Asp Val Arg Gln Gly Ala Lys Lys
    50                  55                  60

Gly Tyr Asn Cys Asp Met Phe Ile Ser Leu His Met Asn Ala Ser Asp
65                  70                  75                  80

Gly Arg Gly Asn Gly Thr Glu Ala Trp Val Ala Arg Ser Ala Arg Ser
                85                  90                  95

Ser Ile Lys Glu Ile Ala Ser Arg Leu Cys Lys Asn Tyr Ala Thr Leu
        100                 105                 110

Gly Leu Gln Asn Arg Gly Val Lys Glu Lys Asn Tyr Trp Glu Met Thr
            115                 120                 125

Asp Thr Asn Cys Pro Asn Ile Ile Phe Glu Thr Met Phe Cys Asp Asp
        130                 135                 140

Lys His Asp Ile Asp Ile Trp Ala Ser Thr Ser Trp Asp Lys Leu Ala
145                 150                 155                 160

Arg Leu Ile Ala Asn Ala Ile Asp Pro Asn Ile Pro Leu Glu Lys Glu
                165                 170                 175

Gln Asp Tyr Tyr Arg Val Cys Val Gln Arg Phe Thr Asn Lys Glu Asp
            180                 185                 190

Ala Glu Lys Ala Gln Gln Arg Ile Ser Asn Glu Leu Gly Tyr Tyr Cys
        195                 200                 205

Phe Ala Glu Lys Ile
        210

<210> SEQ ID NO 4
<211> LENGTH: 642
<212> TYPE: DNA
<213> ORGANISM: Bacteriophage CP390

<400> SEQUENCE: 4
atgaaaatag ctttaagagg tggacattca cctaattgca aaggtgctaa cgttttaaga      60
gatgagcaat cttgcatgtg ggctttagct gatgaagtag aaaaagtttt aacctctcat    120
ggtcataccg ttgtaagatg tgaaacaact ttatcaaatg aaagagaaga tgtaagacaa    180
ggggctaaaa aaggttataa ttgcgatatg tttatctctc ttcacatgaa tgcaagtgac    240
ggtcgaggaa atggcacgga agcgtgggtt gctagaagtg cgagaagttc tataaaagaa    300
attgcttcaa gattatgcaa aaactatgca actttaggat tgcaaaacag aggtgtaaaa    360
gagaagaatt actgggaaat gacagataca aattgcccta atattatttt tgaaactatg    420
ttctgtgatg ataagcatga tatagatata tgggcttcaa cctcttggga taaattagcg    480
agattaatcg caaatgctat cgaccctaat ataccactag aaaaggaaca agactattat    540
agagtgtgta caaaagatt tacaaataaa gaagatgcag aaaaagcgca acaaagaata    600
agcaatgagc taggttatta ttgctttgcc gaaaagatat ag                        642

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
taccatggtg ataattggaa gtagatat                                         28

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6

```
gtggtgctcg agtatctttt cggcaaagca at                              32

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
gcactacata tgaaaatagc tttaagaggt gga                              33

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
gtggtgctcg agtatctttt cggcaaagca at                              32
```

BACTERIOPHAGE LYTIC ENZYMES AS ALTERNATIVE ANTIMICROBIALS

FIELD OF THE INVENTION

The invention relates to Bacteriophage lytic enzymes or functional fragments thereof useful for controlling *Clostridium perfringens* bacteria and uses of said lytic enzymes including, but not limited to compositions and methods of treating diseases caused by the *C. perfringens*.

BACKGROUND OF THE INVENTION

*Clostridium perfringens* is a Gram-positive, rod-shaped, anaerobic, spore-forming bacterium of the genus *Clostridium*. *C. perfringens* is ubiquitous in nature and is typically found as a component of decaying vegetation, marine sediment, the intestinal tract of humans and other vertebrates, insects, and soil. Although ubiquitous, and often benign, *C. perfringens* is also the cause of many severe infections of animals and humans. Indeed, *C. perfringens* is known to be the cause of food poisoning, gas gangrene (clostridial myonecrosis), necrotic enteritis, and non-foodborne gastrointestinal infections. Thus, *C. perfringens* is a pathogen in both humans and animals (Songer, 1997). Although all domestic animals, can be infected, *C. perfringens* is a particular concern for the poultry industry. Indeed, it is in poultry species that *C. perfringens* causes the most devastating losses.

In chickens, *C. perfringens* causes necrotic enteritis, the most common and financially devastating bacterial disease in modern broiler flocks. Although the clinical illness is usually very short, mortality in an unprotected poultry flock can be devastating. Indeed, often the only sign of necrotic enteritis in a flock is a sudden increase in mortality. In addition to increased mortality, necrotic enteritis may present as birds with depression, ruffled feathers, and dark diarrhea. Typically the disease persists in a flock for between about 5-10 days, with mortality between about 2-50%.

Typically necrotic enteritis is controlled by antimicrobial drugs administered at prophylactic doses either in water or in feed. However, there is increasing public opposition to the use of antibiotics in animal feeds. For example, in Europe, antibiotics are already banned from animal feeds (see e.g., van Immerseel et al., 2004, 2008). The same could be soon be true for the United States. Without traditional antibiotics for the prevention of necrotic enteritis and other diseases caused by *C. perfringens*, such diseases could potentially become a far greater problem for the poultry industry.

Therefore, what is needed in the art are alternatives to traditional antibiotics which are effective in preventing and treating disease caused by *C. perfringens*, especially *C. perfringens* that affect poultry.

Fortunately, as will be clear from the following disclosure, the present invention provides for these and other needs.

SUMMARY OF THE INVENTION

In one embodiment, the present invention provides an isolated An isolated *Clostridium perfringens* bacteriophage lytic enzyme, wherein the bacteriophage lytic enzyme is a member selected from the group consisting of a CP26F lysin and a CP39O lysin, and wherein, the bacteriophage lytic enzyme activity results in lysis of *Clostridium perfringens* bacterial cells. In one exemplary embodiment, the isolated *Clostridium perfringens* bacteriophage lytic enzyme comprises a peptide having an amino acid sequence that is at least about 90% identical to SEQ ID NO:1. In another exemplary embodiment, the isolated *Clostridium perfringens* bacteriophage lytic enzyme has a sequence according to SEQ ID NO:1. In another exemplary embodiment, the isolated *Clostridium perfringens* bacteriophage lytic enzyme comprises a peptide having an amino acid sequence that is at least about 90% identical to SEQ ID NO:3. In still another exemplary embodiment, the isolated *Clostridium perfringens* bacteriophage lytic enzyme has a sequence according to SEQ ID NO:3. In still another exemplary embodiment, the isolated *Clostridium perfringens* bacteriophage lytic enzyme is isolated from a *Clostridium perfringens* bacteriophage that is a member selected from the group consisting of *Clostridium perfringens* Bacteriophage CP39O having an ATCC deposit designation PTA-11081 and *Clostridium perfringens* Bacteriophage CP26F having an ATCC deposit designation PTA-11080.

In another embodiment, the present invention provides an isolated nucleic acid molecule that encodes a *Clostridium perfringens* bacteriophage lytic enzyme, wherein the bacteriophage lytic enzyme is a member selected from the group consisting of a CP26F lysin and a CP39O lysin, and wherein, the bacteriophage lytic enzyme activity results in lysis of *Clostridium perfringens* bacterial cells. In one exemplary embodiment, the isolated nucleic acid molecule is a member selected from the group consisting of an isolated nucleic acid that encodes a peptide having an amino acid sequence that is at least about 90% identical to SEQ ID NO:1 and an isolated nucleic acid that encodes a peptide having an amino acid sequence that is at least about 90% identical to SEQ ID NO:3. In another exemplary embodiment, the isolated nucleic acid molecule encodes a peptide having an amino acid sequence according to SEQ ID NO:1. In another exemplary embodiment, the isolated nucleic acid molecule encodes a peptide having an amino acid sequence according to SEQ ID NO:3.

In another embodiment, the present invention provides an antimicrobial composition effective against *Clostridium perfringens* comprising a *Clostridium perfringens* bacteriophage lytic enzyme, wherein the bacteriophage lytic enzyme is a member selected from the group consisting of a CP26F lysin and a CP39O lysin, and wherein, the bacteriophage lytic enzyme activity results in lysis of *Clostridium perfringens* bacterial cells. In one exemplary embodiment, the antimicrobial composition comprises a peptide having an amino acid sequence that is at least about 90% identical to SEQ ID NO:1. In another exemplary embodiment, the antimicrobial composition comprises a peptide that has a sequence according to SEQ ID NO:1. In another exemplary embodiment, the antimicrobial composition comprises a peptide having an amino acid sequence that is at least about 90% identical to SEQ ID NO:3. In still another exemplary embodiment, the antimicrobial composition comprises a peptide that has a sequence according to SEQ ID NO:3. In another exemplary embodiment, the antimicrobial composition comprises a bacteriophage lytic enzyme that is isolated from a *Clostridium perfringens* bacteriophage that is a member selected from the group consisting of *Clostridium perfringens* Bacteriophage CP39O having ATCC deposit designation PTA-11081 and *Clostridium perfringens* Bacteriophage CP26F having ATCC deposit designation PTA-11080.

In another embodiment, the present invention provides an animal feed comprising a *Clostridium perfringens* bacteriophage lytic enzyme, wherein the bacteriophage lytic enzyme is a member selected from the group consisting of a CP26F lysine and a CP39O lysin, and wherein the bacteriophage lytic enzyme is present in an amount effective for controlling *Clostridium perfringens* infection in livestock. In one exemplary embodiment, the animal feed is suitable for feeding to chickens.

Other features, objects and advantages of the invention will be apparent from the detailed description which follows.

BRIEF DESCRIPTION OF THE DRAWINGS

FIG. 1. SEQ ID NO:1: Bacteriophage CP26F lysin amino acid sequence.

FIG. 2. SEQ ID NO:2: Exemplary nucleic acid sequence that encodes a bacteriophage CP26F lysin. Underlined sequences are the "start" and "stop" sites for the respective genes.

FIG. 3. SEQ ID NO:3: Bacteriophage CP39O lysin amino acid sequence.

FIG. 4. SEQ ID NO:4: Exemplary nucleic acid sequence that encodes a Bacteriophage CP39O lysin. Underlined sequences are the "start" and "stop" sites for the respective genes FIG. 5. Comparative alignment of the amino acid sequences of CP26F lysin and CP39O lysin.

DETAILED DESCRIPTION OF THE INVENTION

Definitions

The term "livestock" as used herein refers to one or more domesticated animals raised in an agricultural setting typically, though not necessarily, for the production of food, fiber, or labor. Exemplary livestock species include, but are not limited to cattle, swine, sheep and poultry.

The term "poultry" as used herein, refers to domestic fowl, e.g., chickens, turkeys, guinea fowl, ducks, geese, quails, pigeons, game birds e.g., pheasants, partridges ratites, etc, that are reared or kept in captivity for breeding, the production of meat or eggs, or for restocking supplies of game.

The term "antimicrobial", "microbicide" or any other grammatically equivalent expression as used herein, refers to any composition and/or substance that is effective for the control of microorganisms e.g., bacteria, e.g., *Clostridium perfringens*. In an exemplary embodiment, an "antimicrobial" is an antimicrobial composition comprising a bacteriophage lytic enzyme effective for control of *Clostridium perfringens*.

As used herein, the term "control" or "controlling" as in e.g., the phrase: the "control" of *Clostridium perfringens*, "controlling" *Clostridium perfringens*, "controlling *Clostridium perfringens* populations", or "controlling *Clostridium perfringens* infection" or any grammatically equivalent expression, refers to any means for preventing infection or infestation, reducing or diminishing the population of already infected areas or organisms, or elimination of the population of *Clostridium perfringens* or other species whose "control" is desired. Indeed, "controlling" as used herein refers to any indica of success in prevention, elimination, reduction or amelioration of *Clostridium perfringens*, a *Clostridium perfringens* infection, or a population of *Clostridium perfringens*.

The expression "*Clostridium perfringens* infection" as used herein refers to the acquisition of a *Clostridium perfringens* microorganism into or onto the body of a "host". In one exemplary embodiment, a "host" is an animal e.g., a chicken. In another exemplary embodiment, a "host" is a human. A "*Clostridium perfringens* infection" may or may not lead to disease. The expression "disease" as used herein, refers to a particular case of *Clostridium perfringens* infection wherein a host, having acquired *Clostridium perfringens* into or onto its body, interacts with the *Clostridium perfringens* in such a way as to result in host damage that has outward manifestations e.g., clinical symptoms of disease, e.g., increased mortality in a population, depression, ruffled feathers, and dark diarrhea, etc.

The phrase "effective amount" or "amount effective to" or any other grammatically equivalent expression as used herein, refers to the amount of a substance e.g., an antimicrobial bacteriophage lytic enzyme as disclosed herein, that is effective to control *Clostridium perfringens*. A person of ordinary skill in the art will be able without undue experimentation, having regard to that skill and this disclosure, to determine an effective amount of an antimicrobial bacteriophage lytic enzyme for practice of the *Clostridium perfringens* control methods disclosed herein. For example, a particular antimicrobial bacteriophage lytic enzyme may be more effective at higher or lower doses. By evaluating livestock e.g., poultry, e.g., chickens, using the methods described herein, a skilled practitioner will be able to determine whether said livestock is responding to treatment and will know how to adjust the dosage levels accordingly.

The term "prevent" or "prevention" as used herein, refers to any indica of success in prevention, or amelioration of disease or infection, including any objective or subjective parameter such as abatement, remission, and/or diminishing of symptoms. For example, the terms "prevent" or "prevention" as used herein, refer to the prevention of disease associated with *Clostridium perfringens*; reduction in the severity of disease associated with *Clostridium perfringens*; reduction in expected deaths or in the death rate of livestock e.g., poultry, e.g., chickens suffering from disease associated with *Clostridium perfringens*. In an exemplary embodiment, success in the prevention of disease associated with *Clostridium perfringens* is measured by comparing the symptomology, morbidity and/or mortality in poultry fed, or otherwise treated with, antimicrobial bacteriophage lytic enzymes as compared to the symptomology, morbidity and/or mortality in poultry that are not fed, or otherwise treated with, antimicribial bacteriophage lytic enzymes, and observing that the severity or occurrence of symptoms and/or the morbidity and/or mortality of poultry is lessened, diminished and therefore reduced by comparison to poultry not fed, or otherwise treated with antimicrobial bacteriophage lytic enzymes. The prevention, treatment, reduction or amelioration of symptoms can be based on objective or subjective parameters; including the results of physical examination, biopsy or microscopic examination of a tissue sample, or any other appropriate means known in the art.

The term "necrotic enteritis" as used herein, refers to an acute or chronic enterotoxemia disease that typically affects poultry e.g., chickens, turkeys and ducks. The condition occurs worldwide and is caused by *Clostridium perfringens*. The disease is characterised inter alia by a fibrino-necrotic enteritis, usually of the mid-small intestine.

The term "biological sample" or the term "diagnostic sample" as used herein, refers to any sample obtained from a living or dead organism. Examples of biological samples include isolated organs or body parts e.g., isolated spleen, trachea, thymus; mucosa, swabs e.g., cloacal swabs oropharyngeal swabs.

The term "*Clostridium perfringens* bacteriophage lytic enzyme" or "bacteriophage lytic enzyme" or "lytic enzyme" or "bacteriophage lysin" or "lysin" "bacteriophage endolysin" or "endolysin" as used herein, refers to lytic enzymes that cleave or are capable of cleaving a peptide moiety that comprises a bacterial peptidoglycan cell wall, at an amide bond located between an N-acetylmuramic acid and an L-alanine of the peptide moiety and thereby, causing lysis of *Clostridium perfringens* bacterium. In an exemplary embodiment, a *Clostridium perfringens* bacteriophage lytic enzyme comprises an amino acid sequence that is at least about 90% identical to amino acids 1-158 of SEQ ID NO:1. In one exemplary embodiment, a "*Clostridium perfringens* bacteriophage lytic enzyme" or "bacteriophage lytic enzyme" is a CP26F lysin (plyCP26F) that is derived from bacteriophage CP26F, which was deposited on Jun. 23, 2010 with the American Type Culture Collection (ATCC) under the provisions of the Budapest Treaty and assigned the Deposit Designation PTA-11080, that cleaves or is capable of cleaving a peptide moiety that comprises a bacterial peptidoglycan cell wall, at an amide bond located between an N-acetylmuramic acid and an L-alanine of the peptide moiety thereby causing lysis of *Clostridium perfringens* bacterium wherein the CP26F lysin comprises an amino acid sequence that is at least about 91% identical to amino acids 1-158 of SEQ ID NO:1. In other exemplary embodiments a "*Clostridium perfringens* bacteriophage lytic enzyme" is a CP26F lysin and comprises an amino acid sequence that is at least about 92%, 93%, 94%, 95%, 96%, 97%, 98%, 99%, 100%, identical to amino acids 1-158 of SEQ ID NO:1. In one exemplary embodiment, a "*Clostridium perfringens* bacteriophage lytic enzyme" is a CP26F lysin and has an amino acid sequence that is at least about 90%, 91%, 92%, 93%, 94%, 95%, 96%, 97%, 98%, 99%, identical to amino acids 1-212 of SEQ ID NO:1. In another exemplary embodiment, a "*Clostridium perfringens* bacteriophage lytic enzyme" is a CP26F lysin that cleaves or is capable of cleaving a peptide moiety that comprises a bacterial peptidoglycan cell wall, at an amide bond located between an N-acetylmuramic acid and an L-alanine of the peptide moiety thereby causing lysis of *Clostridium perfringens* bacterium wherein the CP26F lysine has an amino acid sequence according to SEQ ID NO:1. In another exemplary embodiment, a *Clostridium perfringens* bacteriophage lytic enzyme comprises an amino acid sequence that is at least about 90% identical to amino acids 1-158 of SEQ ID NO:3. In one exemplary embodiment, a "*Clostridium perfringens* bacteriophage lytic enzyme" or "bacteriophage lytic enzyme" is a CP39O lysin (plyCP39O) derived from bacteriophage CP39O, which was deposited on Jun. 23, 2010 with the American Type Culture Collection (ATCC) under the provisions of the Budapest Treaty and assigned the Deposit Designation PTA-11081, that cleaves or is capable of cleaving a peptide moiety that comprises a bacterial peptidoglycan cell wall at an amide bond located between an N-acetylmuramic acid and an L-alanine of the peptide moiety thereby causing lysis of *Clostridium perfringens* bacterium wherein the CP39O lysin comprises an amino acid sequence that is at least about 91% identical to amino acids 1-158 of SEQ ID NO:3. In other exemplary embodiments a "*Clostridium perfringens* bacteriophage lytic enzyme" is a CP39O lysin that cleaves or is capable of cleaving a peptide moiety that comprises a bacterial peptidoglycan cell wall, at an amide bond located between an N-acetylmuramic acid and an L-alanine of the peptide moiety thereby causing lysis of *Clostridium perfringens* bacterium wherein the CP39O lysin wherein the CP39O lysine comprises an amino acid sequence that is at least about 92%, 93%, 94%, 95%, 96%, 97%, 98%, 99%, 100%, identical to amino acids 1-158 of SEQ ID NO:3. In one exemplary embodiment, a "*Clostridium perfringens* bacteriophage lytic enzyme" is a CP39O lysin and has an amino acid sequence that is at least about 90%, 91%, 92%, 93%, 94%, 95%, 96%, 97%, 98%, 99%, identical to amino acids 1-212 of SEQ ID NO:3. In another exemplary embodiment, a "*Clostridium perfringens* bacteriophage lytic enzyme" is a CP39O lysin and has an amino acid sequence according to SEQ ID NO:3.

*Clostridium perfringens* bacteriophage lytic enzymes can be isolated from any source and/or can be synthetically made, by methods known on the art (see e.g., R. B. Merrifield (1963) *J. Am. Chem. Soc.* 85 (14): 2149-2154, U.S. Pat. No. 4,192,798; U.S. Pat. No. 5,763,284; U.S. Pat. No. 5,942,609; etc) as long as they are substantially identical to *Clostridium perfringens* bacteriophage lytic enzyme sequences as disclosed herein and are able to cleave a peptide moiety comprising the bacterial peptidoglycan cell wall of *Clostridium perfringens* species, at an amide bond located between an N-acetylmuramic acid and an L-alanine of the peptide moiety thereby causing lysis of *Clostridium perfringens* bacterial cells. Methods for determining nucleotide and/or amino acid sequence identity and "substantial identity" are described below.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In one exemplary embodiment, an isolated *Clostridium perfringens* bacteriphage lytic enzyme nucleic acid e.g., a 26F lytic enzyme, is separated from open reading frames and/or other nucleic acid sequences that flank the bacteriphage lytic enzyme nucleic acid in its native state. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide" and "protein" are used interchangeably herein to refer to a polymer of amino acid residues. The terms apply to naturally occurring amino acid polymers and non-naturally occurring amino acid polymers as well as amino acid polymers in which one or more amino acid residues is an artificial chemical mimetic of a corresponding naturally occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, Proteins (1984)). Such conservatively modified variants are in addition to and do not exclude polymorphic variants, interspecies homologs, and alleles.

The following eight groups illustrate some exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Macromolecular structures such as polypeptide structures are described in terms of various levels of organization. For a general discussion of this organization, see, e.g., Alberts et al., Molecular Biology of the Cell ($3^{rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "label" as used herein, refers to a composition detectable by spectroscopic, photochemical, biochemical, immunochemical, or chemical means. Exemplary labels include $^{32}$P, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "labeled nucleic acid probe or oligonucleotide" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically DNA oligonucleotides of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5©1991, Whitehead Institute for Biomedical Research, Cambridge, Mass.). One of skill in the art will appreciate that the specificity of a particular probe or primer increases with its length. Thus, for example, a primer comprising 20 consecutive nucleotides of a *Clostridium perfringens* bacteriophage lytic enzyme sequence will anneal to a related target sequence with a higher specificity than a corresponding primer of only 15 nucleotides. Thus, in an exemplary embodiment, greater specificity of a nucleic acid primer or probe, is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994, John Wiley & Sons). The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, over expressed, under expressed or not expressed at all.

The term "promoter" or "promoter complex" or "promoter sequence" as used herein refers to an array of nucleic acid expression control sequences that direct transcription of a nucleic acid. As used herein, a "promoter" or "promoter complex" or "promoter sequence" comprises necessary nucleic acid sequences near the start site of transcription, such as, e.g., a polymerase II type promoter, a TATA element etc to "control" transcription of an operably linked nucleic acid. In some exemplary embodiments, a "promoter complex" or "promoter sequence" also includes distal enhancer or repressor elements, which can be, but are not necessarily located as much as several thousand base pairs from the start site of transcription. In other exemplary embodiments, "promoter" or "promoter complex" or "promoter sequence" includes sequences that facilitate transcription of an operably linked heterologous nucleic acid and/or expression of the final protein product of the heterologous nucleic acid e.g., intron sequence and/or intron and ubiquitin monomer sequences as disclosed herein.

As is well known in the art, a "constitutive" promoter is a promoter that is active under most environmental and developmental conditions. An "inducible" promoter is a promoter that is active under environmental or developmental regulation, e.g., upregulation in response to temperature. Promoters may be derived in their entirety from a native gene, may comprise a segment or fragment of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of a *Clostridium perfringens* bacteriophage lytic enzyme. Hybridization of the first and second nucleic acids is conducted under standard stringent conditions, e.g., high temperature and/or low salt content, which tend to disfavor hybridization of dissimilar nucleotide sequences.

The term "operably linked" refers to a functional linkage between a nucleic acid expression control sequence (such as e.g., an array of transcription factor binding sites) and a second nucleic acid sequence (such as e.g., *Clostridium perfringens* bacteriophage lytic enzyme nucleic acid sequence), wherein the expression control sequence directs expression e.g., transcription, of the nucleic acid corresponding to the second sequence. In an exemplary embodiment, a promoter that is "operably linked" to a heterologous nucleic acid e.g., a *Clostridium perfringens* bacteriophage lytic enzyme, is located upstream of and in-frame with the heterologous nucleic acid.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" as used herein, refers to a nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed e.g., *Clostridium perfringens* bacteriophage lytic enzyme, e.g., a 26F lytic enzyme sequence, 39O lytic enzyme sequence, etc, operably linked to a promoter.

Typically, an "expression cassette" is part of an "expression vector". The term "vector" as used herein, refers to nucleic acid capable of replicating in a selected host cell or organism. A vector can replicate as an autonomous structure, or alternatively can integrate into the host cell chromosomes and thus replicate along with the host cell genome. Thus, an "expression vector" is a nucleic acids capable of replicating in a selected host cell or organism e.g., a plasmid, virus, artificial chromosome, nucleic acid fragment, or any suitable construct known in the art, which comprises an "expression cassette".

The term "transformation" as used herein encompasses any and all techniques by which a nucleic acid molecule might be introduced into a cell, including but not limited to, transfection with viral vectors, transformation with plasmid vectors, and introduction of naked DNA by electroporation, lipofection, *Agrobacterium* infection, and particle gun acceleration.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length *Clostridium perfringens* bacteriophage lytic enzyme sequence or gene sequence given in a sequence listing, or may comprise a complete *Clostridium perfringens* bacteriophage lytic enzyme sequence or gene sequence.

The terms "identical" or percent "identity," in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403- 410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl.

Acad. Sci. USA 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

I. Introduction:

*Clostridium perfringens* is a Gram-positive anaerobic spore-forming bacterium that produces toxins which can cause disease symptoms and pathogenesis in a variety of animals, humans and poultry.

In the United States *C. perfringens* bacteria are reported by the Centers for Disease Control and Prevention (CDC) as the third most common cause of food-borne illness, with economic costs estimated to exceed $120 million per year. Poorly prepared meat and poultry are believed to be the main sources of *C. perfringens* poisoning in humans (see e.g., Centers for Disease Control and Prevention (CDC). *Surveillance for foodborne disease outbreaks*—United States, 2006 and *MMWR Morb Mortal Wkly Rep.* 2009, 58, 609-615).

In addition to causing foodborne illness in humans, *Clostridium perfringens* is also an important disease agent of poultry and livestock. In chickens *C. perfringens* is the etiologic agent of necrotic enteritis. Necrotic enteritis is an acute or chronic enterotoxemia typically characterized by necrotic lesions in the small intestines of poultry. Clinical signs of necrotic enteritis include e.g., diarrhea, dehydration, and decreased feed consumption that can lead to death. Frighteningly for poultry producers, severe acute cases can have mortality rates as high as 50%.

Sub-clinical infections also harm poultry producers as sub-clinical infection in poultry may cause damage the intestinal mucosa of the poultry species e.g., chickens, thereby resulting in decreased nutrient absorption, limited weight gain and increased feed conversion ratio.

Necrotic enteritis is typically controlled by antibiotics added to feed. However, there is evidence that the use of antibiotics in animal feed can lead to antibiotic resistance among human bacterial pathogens (see e.g., Chapin et al., (2005) *Fundam. Applied Toxicol.*, 29: 1-17). Furthermore, some countries have already banned the use of antibiotics in animal feed even though these same countries as a result have experienced increases in clostridial necrotic enteritis as well as other animal health problems (see e.g., Casewell et al., (2003) *Journal of Antimicrobial Chemotherapy* 52, 159-16).

Therefore, there is clearly a need in the art for improved control of *Clostridium perfringens*. Furthermore, there is a need to develop alternative antimicrobials as substitutes or to complement currently used antibiotics to control *Clostridium perfringens* as well as other disease-causing pathogens in animals and humans.

Thus, in one exemplary embodiment, the invention provides isolated *Clostridium perfringens* bacteriophage lytic enzyme sequences including, but not limited to amino acid sequences and nucleic acid sequences which encode enzymes that are capable of cleaving a peptide moiety comprising a bacterial peptidoglycan cell wall at an amide bond located between an N-acetylmuramic acid and an L-alanine of the peptide moiety and thereby, causing lysis of *Clostridium perfringens* bacteria. Thus, in some exemplary embodiments of the invention the disclosed bacteriophage lytic enzymes are effective for controlling *Clostridium perfringens* bacteria.

Thus, in one exemplary embodiment, the invention provides methods for controlling *Clostridium perfringens* using isolated *Clostridium perfringens* bacteriophage lytic enzymes disclosed herein.

II. Isolating Bacteriophage Lytic Enzymes and Constructing Expression Vectors

A. General Methods

This invention utilizes routine techniques in the field of recombinant genetics. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)). Unless otherwise noted, technical terms are used according to conventional usage. Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

Methods disclosed herein may also utilize routine techniques in the field of microbiology. Basic texts disclosing the general methods of use in this invention include, e.g., *Methods for General and Molecular Microbiology*, 3rd Edition, C. A. Reddy, et al., eds. ASM Press (2008); and *Encyclopedia of Microbiology*, 2nd ed., Joshua Lederburg, ed., Academic Press (2000).

Unless otherwise noted, technical terms are used according to conventional usage. Definitions of common terms in microbiology maybe found in e.g., *Microbiology* By Cliffs Notes, I. Edward Alcamo, Wiley (1996); Encyclopedia of Microbiology, (2000) supra; Singleton et al., Dictionary of Microbiology and Molecular Biology (2d ed. 1994). Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

B. Methods for the Isolation of Nucleic Acids Comprising *Clostridium perfringens* Bacteriophage Lytic Enzyme Sequences

*Clostridium perfringens* bacteriophage lytic enzyme nucleic acids can be isolated using any of a variety of methods known to those of skill in the art which may be used for isolation of bacterial nucleic acid sequences. For example, *Clostridium perfringens* bacteriophage lytic enzyme nucleic acids can be isolated from genomic DNA fragments encoding a *Clostridium perfringens* bacteriophage lytic enzyme nucleic acids gene e.g., a 26F lytic enzyme gene, a 39O lytic enzyme gene, etc. An exemplary "*Clostridium perfringens* bacteriophage lytic enzyme gene" is shown in FIG. 2. Another exemplary "*Clostridium perfringens* bacteriophage lytic enzyme gene" is shown in FIG. 4. The term "*Clostridium perfringens* bacteriophage lytic enzyme gene fragment" or "*Clostridium perfringens* bacteriophage lytic enzyme gene fragment" refers to a portion of a *Clostridium perfringens* bacteriophage lytic enzyme gene which is less than the entire promoter and coding regions of the gene. Genomic fragments encoding *Clostridium perfringens* bacteriophage lytic enzymes e.g., 26F lytic enzyme and *Clostridium perfringens* bacteriophage lytic enzyme gene fragments can be prepared as disclosed below.

In an exemplary embodiment, the nucleic acid sequences comprising *Clostridium perfringens* bacteriophage lytic enzyme nucleic acid sequences and related nucleic acid sequences are cloned from genomic DNA libraries using labeled oligonucleotide probes. In another exemplary embodiment, the nucleic acid sequences comprising *Clostridium perfringens* bacteriophage lytic enzyme nucleic acid sequences and related nucleic acid sequences are cloned from genomic DNA libraries using amplification techniques and labeled oligonucleotide primers.

*Clostridium perfringens* bacteriophage lytic enzyme nucleic acids typically comprise sequences that are identical to, or show substantial sequence identity (as defined above) to nucleotides 1-642 of the nucleic acid sequence depicted in SEQ ID NO:2 or to nucleotides 1-642 of the nucleic acid sequence depicted in SEQ ID NO:4.

Thus, *Clostridium perfringens* bacteriophage lytic enzyme typically hybridize to base pairs 1-642 of the nucleic acid sequence of SEQ ID NO:2 or SEQ ID NO:4 under stringent hybridization conditions.

To prepare a genomic library, typically DNA is extracted from the organism of interest and either mechanically sheared or enzymatically digested to yield fragments of about 15-20 kb. The fragments are then separated by gradient centrifugation from undesired sizes and are constructed in bacteriophage lambda vectors. These vectors and phage are packaged in vitro, as described e.g., in Sambrook, et al. supra. Recombinant phage are analyzed by plaque hybridization as described in Benton and Davis, Science, 196:180-182 (1977). Colony hybridization is carried out as generally described in M. Grunstein et al. Proc. Natl. Acad. Sci. USA., 72:3961-3965 (1975). DNA encoding *Clostridium perfringens* bacteriophage lytic enzyme genes and/or *Clostridium perfringens* bacteriophage lytic enzyme gene fragments is identified in genomic libraries by its ability to hybridize with labeled nucleic acid probes that comprise *Clostridium perfringens* bacteriophage lytic enzyme sequences, e.g., on Southern blots. The hybridizing DNA regions are isolated by standard methods familiar to those of skill in the art. See e.g., Sambrook, et al. supra.

In an exemplary embodiment, *Clostridium perfringens* bacteriophage lytic enzyme sequences are isolated by screening DNA libraries with labeled oligonucleotide probes having sequences derived from nucleotides 1-642 of the DNA sequence of the *Clostridium perfringens* CP26F bacteriophage lytic enzyme shown in FIG. 2, SEQ ID NO:2. In another exemplary embodiment, *Clostridium perfringens* bacteriophage lytic enzyme sequences are isolated by screening DNA libraries with labeled oligonucleotide probes having sequences derived from nucleotides 1-642 of the DNA sequence of the *Clostridium perfringens* CP39O bacteriophage lytic enzyme shown in FIG. 4, SEQ ID NO:4.

In still another exemplary embodiment, *Clostridium perfringens* bacteriophage lytic enzyme sequences are isolated by screening and analysis of analyses of phage genomes.

Other methods known to those of skill in the art can also be used to isolate DNA fragments comprising *Clostridium perfringens* bacteriophage lytic enzyme sequences. See e.g., Sambrook, et al. for a description of other techniques for the isolation of DNAs related to DNA molecules of known sequence.

Sequence Features of *Clostridium perfringens* Bacteriophage Lytic Enzyme Sequences A full length bacteriophage lytic enzyme typically comprises about 642 nucleotides. The sequence of a full length CP26F bacteriophage lytic enzyme is shown in FIG. 2 as SEQ ID NO:2. The sequence of a full length CP26F bacteriophage lytic enzyme is shown in FIG. 4 as SEQ ID NO:4.

CP26F and CP39O bacteriophage lytic enzymes disclosed herein have high overall sequence similarity. However, the similarity is unevenly distributed over the length of the sequence. For example, predicted protein amino acid sequences were identical at the C-terminus cell-wall binding domain, but shared only 56 percent identity to each other at the N-terminal catalytic domain. Specifically, residues 164 through 213 of PlyCP39O were identical to residues 163 through 212 of PlyCP26F encoding the cell wall binding domain. The variable N-terminal regions of the proteins to position 162 are both N-acetylmuramoyl-L-alanine amidases.

C. Construction of Vectors Comprising Bacteriophage Lytic Enzyme Sequences

Once a *Clostridium perfringens* bacteriophage lytic enzyme sequence has been isolated, various methods may be used to construct expression cassettes, vectors and other DNA constructs. Expression cassettes comprising a *Clostridium perfringens* bacteriophage lytic enzyme sequence can be constructed in a variety of ways. The skilled artisan is well aware of the genetic elements that must be present on an expression construct/vector in order to successfully transform, select and propagate the expression construct in host cells. Techniques for manipulation of nucleic acids encoding *Clostridium perfringens* bacteriophage lytic enzyme sequences such as subcloning nucleic acid sequences into expression vectors, labeling probes, DNA hybridization, and the like are described generally in Sambrook, et al., supra.

DNA constructs comprising *Clostridium perfringens* bacteriophage lytic enzyme operably linked to heterologous DNA sequences can be inserted into a variety of vectors. Typically, the vector chosen is an expression vector that is useful in the transformation of bacteria e.g., *Escherichia coli*. The expression vector may be a plasmid, virus, cosmid, artificial chromosome, nucleic acid fragment, or the like. Such vectors can be constructed by the use of recombinant DNA techniques well known to those of skill in the art. The expression vector comprising *Clostridium perfringens* bacteriophage lytic enzyme sequence may then be transfected/transformed into the target host cells. Successfully transformed cells are then selected based on the presence of a suitable marker gene as disclosed below.

A number of recombinant vectors are available to those of skill in the art for use in the stable transfection of bacteria and other microorganisms (see e.g., Sambrook, et al., supra). Appropriate vectors are readily chosen by one of skill in the art. In an exemplary embodiment, known vectors are used to create expression constructs comprising *Clostridium perfringens* bacteriophage lytic enzyme sequences.

Typically, transformation vectors include one or more cloned *Clostridium perfringens* bacteriophage lytic enzyme genes (or cDNAs) operably linked to promoter sequences, and a selectable marker. Such transformation vectors also typically include a transcription initiation start site, a heterologous nucleic acid the control of whose expression is desired, a ribosome binding site, an RNA processing signal, a transcription termination site, and/or a polyadenylation signal.

(i) Regulatory Elements

In addition to *Clostridium perfringens* bacteriophage lytic enzyme sequence or a derivative thereof, expression constructs prepared as disclosed may comprise additional elements. In an exemplary embodiment, expression constructs comprising a *Clostridium perfringens* bacteriophage lytic enzyme sequences also comprise an enhancer sequence such that the expression of the heterologous protein may be enhanced. As is known in the art, enhancers are typically found 5' to the start of transcription, they can often be inserted in the forward or reverse orientation, either 5' or 3' to the coding sequence.

(ii) Marker Genes

As noted above, transformation/expression vectors typically include a selectable and/or screenable marker gene to allow for the ready identification of transformants. Exemplary selectable marker genes include, but are not limited to those encoding antibiotic resistance (e.g. resistance to kanamycin, ampicillin, etc). Exemplary screenable markers include e.g., an introduced six amino acid histidine tag at the C-terminus of the recombinant protein.

In an exemplary embodiment, a selectable or screenable marker gene is employed as, or in addition to, a particular gene of interest, to provide or enhance the ability to identify transformants. As is known in the art, "marker genes" are genes that impart a distinct phenotype to cells expressing the marker gene, such that transformed cells can be distinguished from cells that do not have the marker. In one exemplary embodiment, marker genes encode a selectable marker which one can "select" for by chemical means, e.g., through the use of a selective agent (e.g., an antibiotic, or the like). In another exemplary embodiment, marker genes encode a screenable marker, which is identified through observation or testing, e.g., by "screening" (e.g., using an introduced six amino acid histidine tag at the C-terminus of the recombinant protein).

Numerous selectable marker genes are known to the art (see e.g., Sambrook et al, supra).

(iv) Other Vector Components

In some exemplary embodiments, an expression vector further comprises sequences that are joined to the coding sequence of an expressed heterologous nucleic acid, which are removed post-translationally from the initial translation product. In one exemplary embodiment, post-translationally removed sequences facilitate the transport of the protein into or through intracellular or extracellular membranes, thereby facilitating the transport of the protein into compartments inside and/or outside the cell. In an exemplary embodiment, post-translationally removed sequences protect a nascent protein from intracellular proteolytic degradation. In one exemplary embodiment, a nucleic acid segment encoding a leader peptide sequence upstream and in reading frame with a selected coding sequence is used in recombinant expression of the coding sequence in a host cell.

In another exemplary embodiment, an expression construct comprises a bacterial origin of replication, e.g., a ColE1 origin. In still another exemplary embodiment, an expression construct/vector comprises a bacterial selectable marker e.g., an ampicillin, tetracyclin, hygromycin, neomycin or chloramphenicol resistance gene.

As is well known in the art, expression constructs typically comprise restriction endonuclease sites to facilitate vector construction. Exemplary restriction endonuclease recognition sites include, but are not limited to recognition site for the restriction endonucleases NotI, AatII, SacII, PmeI HindIII, PstI, EcoRI, and BamHI.

D. Host Cells, Transformation and Selection Techniques

DNA constructs containing a *Clostridium perfringens* bacteriophage lytic enzyme sequence operably linked to a heterologous DNA sequence e.g., a promoter sequence, can be used to transform cells and produce isolated lysin peptides.

Exemplary host cells for transformation with expression constructs comprising *Clostridium perfringens* bacteriophage lytic enzyme sequences include, but are not limited to e.g., *Escherichia coli*.

The appropriate transformation technique is readily chosen by the skilled practitioner. Exemplary transformation/transfection methods available to those skilled in the art include, but are not limited to: electroporation, calcium chloride transformation and etc., such methods being well known to the skilled artisan (see e.g., Sambrook, supra).

E. Industrial Scale Production: Batch and Continuous Fermentations

In exemplary embodiments, methods for the production of *Clostridium perfringens* bacteriophage lytic enzymes are carried out on an industrial scale.

Generally, to scale up a method for cultivating a microorganism capable of producing isolable amounts of *Clostridium perfringens* bacteriophage lytic enzymes for industrial scale production, the culture of microorganisms is scaled up first to pilot scale (e.g., 0.07, 0.8, 19 m$^3$) and then to production scale (e.g., 57 m$^3$). In one exemplary embodiment, the microorganism capable of producing *Clostridium perfringens* bacteriophage lytic enzymes which is scaled up for industrial production is *Escherichia coli*.

As the skilled artisan will appreciate, significant numbers of fermentations are needed under varying environmental and nutritional conditions to find optimal conditions for scaling up of a particular bioprocess.

Optimization typically begins with shake flasks experiments and is then scaled to in 1- to 100-liter laboratory scale bioreactors (see e.g., Hebbar, K. P., et al. (1997) *Appl. Microbiol. Biotechnol.* 48: 714-719; Tholudur, A. et al., Biotechnol. Bioeng. 66: 1 16 (1999)). To decrease the number of experiments required for optimization, mathematical modeling may be used (see e.g., Alvarez-Ramirez, J. et al., J. Chem. Technol. Biotechnol. 74: 78 84 (1999); Boon, M. A. et al., Biotechnol Bioeng. 64: 558 567 (1999); Cooney, M. J. et al., Biotechnol. Prog. 15: 898 910 (1999); Tholudur A. et al., Biotechnol. Bioeng. 66: 1 16 (1999)).

Scale-up for the growth of microorganisms is usually based on maintaining a constant dissolved oxygen concentration in the liquid (broth), independent of reactor size. Additionally, temperature, pressure, pH, and flow rate must be kept at very specific levels to ensure optimum culture growth, and thus optimum production of product e.g., styrene (see e.g., T. J. Bailey and D. Ollis, *Biochemical Engineering*, 2nd ed., McGraw-Hill, New York, 1987; D. W. Hubbard, L. R. Harris, and M. K. Wierenga, *Chem. Eng. Prog.*, 84 (8), p. 55 (1988); D. C. Wang et al., *Fermentation and Enzyme Technology*, Wiley, New York, (1979); H. Scott Fogler, *Elements of Chemical Kinetics and Reactor Calculations*, Prentice-Hall, New Jersey, (1974); Encyclopedia of Bioprocess Technology, Flickinger, M. C., and Drew, S. W. eds. John Wiley & Sons (2008)).

As is well known in the art, scale-up of a mixing process in fermentation can be broken down into individual, interrelated steps (see e.g., Oldshue, J. Y. (1966) Biotechnol. Bioeng. 8: 3-24). Thereby allowing consideration of the effect of mixing on gas-liquid absorption, fluid shear rates, blending, and heat transfer to be evaluated separately. Since a bioreactor is three-dimensional, one of skill in the art will appreciate the importance of remembering that as the linear dimensions increase, the capacity of the system increases as the cube of the linear dimension. With this increase in scale, other variables rise on the linear scale with different exponents, which may vary from negative to zero to three and higher.

Other factors to consider include, but are not limited to: control of shear stress which, if too great, can cause lysis of cells in culture. Consequently, scale-up and thorough mixing of cells, nutrients, and oxygen need to be carefully balanced. In addition, cells can aggregate, which poses the problems of maintaining a supply of nutrients and removal of wastes.

The skilled artisan having access to this disclosure and the knowledge in the art will be able to determine and optimize a large scale fermentation process for use with the methods disclosed herein. In an exemplary embodiment, the process employs a batch method of fermentation (see e.g., Cinar, A., et al. (2003) *Batch Fermentation: Modeling, Monitoring, and Control* CRC Press). In another exemplary embodiment, the process employs a continuous fermentation process (see e.g., U.S. Pat. No. 4,748,123; Karkare, S. B. et al. (1985) *Bio/Technology* 3, 247-251).

F. Methods for Controlling *Clostridium perfringens*

In some exemplary embodiments, the bacteriophage lytic enzymes disclosed herein are used to treat animals, including humans, infected with *Clostridium perfringens*. Any suitable route of administration can be used to administer the bacteriophage lytic enzymes including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges. Some exemplary uses are disclosed hereinbelow.

(i) Surface Disinfectants:

In some exemplary embodiments, the bacteriophage lytic enzymes disclosed herein, are combined with known surface disinfectants such as e.g., (i) preservatives of various kinds, such as but not limited to benzoic acid and BHT; and (ii) various disinfectants with which the phages are compatible, such as but not limited to quaternary ammonium compounds.

(ii) Antibiotics

In exemplary embodiments, the bacteriophage lytic enzymes disclosed herein are used in combination with known antimicrobial agents (including antibiotics and chemotherapeutic agents) including but not limited to e.g., vancomycin, nisin, danofloxacin and neomycin.

(iii) Surfactants

In exemplary embodiments, the bacteriophage lytic enzymes disclosed herein are used combined with known surfactants and used to treat food processing equipment. The surfactant helps to wet the surface so that the bacteriophage lytic enzymes are distributed over the various surfaces, and to solubilize and remove dirt. Exemplary surfactants include e.g., Tween 80, 20 and 81 and Dobanols.

(iv) Formulation of Livestock Feeds Comprising Bacteriophage Lytic Enzymes

In an exemplary embodiment, animal feed formulations are prepared which comprise bacteriophage lytic enzymes as additives.

In some exemplary embodiments, the bacteriophage lytic enzymes disclosed herein are used to treat animals, by e.g., including them in a feed product. The particular feed product which is used as a vehicle for the delivery of the bacteriophage lytic enzymes will be apparent to those skilled in the art.

In some exemplary embodiments, the bacteriophage lytic enzymes are lyophilized form and are thereafter added to a feed formulation. The dosage of administration for the bacteriophage lytic enzymes is contemplated to be in the range of about 40 mg/kg/day to about 100 mg/per kg/per day. In other exemplary embodiments dosage of administration for the bacteriophage lytic enzymes is contemplated to be about 50 mg/per kg/per day. In other exemplary embodiments dosage of administration for the bacteriophage lytic enzymes is contemplated to be about 60 mg/per kg/per day. In other exemplary embodiments dosage of administration for the bacteriophage lytic enzymes is contemplated to be about 70 mg/per kg/per day. In other exemplary embodiments dosage of administration for the bacteriophage lytic enzymes is contemplated to be about 80 mg/per kg/per day. In other exemplary embodiments dosage of administration for the bacteriophage lytic enzymes is contemplated to be about 90 mg/per kg/per day. The bacteriophage lytic enzymes are administered until successful control of Clostridium perfringens is achieved e.g., until the amount of Clostridium perfringens is substantially reduced.

Although different formulations are prepared for different livestock species, in an exemplary embodiment, feed formulations are prepared which are suitable for feeding to poultry.

The term feed or feed composition means any compound, preparation, mixture, or composition suitable for, or intended for intake by an animal e.g., poultry. In an exemplary embodiment, the bacteriophage lytic enzymes disclosed herein are added directly to the feed. In other exemplary embodiments, bacteriophage lytic enzymes disclosed herein are used in the production of one or more intermediate compositions such as feed additives or premixes that is subsequently added to the feed (or used in a treatment process).

The following examples are offered to illustrate, but not to limit the invention.

EXAMPLES

Example 1

The following example illustrates the isolation of bacteriophages lytic for *Clostridium perfringens.*

Bacterial Hosts, Bacteriophage Isolation and Propagation

*C. perfringens* isolates 39 and 26 were utilized as hosts for propagation of bacteriophage obtained from 0.45 μm filtered offal wash (O) or chicken feces (F) at a local Athens, Ga. chicken processing facility. The host strains were characterized by standard methods and by 16S sequence analysis (Collins et al., 1994; Wise and Siragusa, 2005). Initial screening for bacteriophages lytic for *C. perfringens* was performed on filtered samples obtained from poultry (intestinal material), soil, sewage and poultry processing drainage water. Bacterial viruses capable of lysing strains of *C. perfringens* were identified by spot-testing and titration of strains susceptible to the isolated phages. The *C. perfringens*-specific bacteriophages CP39O and CP26F were propagated by standard procedures (Ackermann and Nguyen, 1983) using the *C. perfringens* isolates 39 and 26 host bacteria cultured (Wise and Siragusa, 2005) using anaerobic chambers. The bacteriophages were subjected to three rounds of plaque purification and consistently suspended in TMGS (10 mM Tris, pH 8, 10 mM Mg++, 0.55% NaCl, 0.1% gelatin). Subsequently, bacteriophages CP39O and CP26F were propagated utilizing a plate lysis method (Helms et al., 1985) under anaerobic conditions for virus purification and DNA extraction.

Purification of bacteriophages, genomic DNA purification and electron microscopy. Genomic DNAs from bacteriophage CP39O, which was deposited on Jun. 23, 2010 with the American Type Culture Collection (ATCC) under the provisions of the Budapest Treaty and assigned the Deposit Designation PTA-11081 and bacteriophage CP26F, which was deposited on Jun. 23, 2010 with the American Type Culture Collection (ATCC) under the provisions of the Budapest Treaty and assigned the Deposit Designation PTA-11080, were purified by two methods. Following plate lysis (see e.g., Helms et al., (1985) DNA. 4:39-49) in anaerobic chambers bacteriophage genomic DNA was purified using the Qiagen™ Lambda Phage DNA Isolation materials. Additionally, bacteriophages were purified from the plate lysates by centrifugation at 4190×g for 20 minutes to remove bacterial debris and low-melt agarose. The clarified supernatant was used to pellet viruses by centrifugation at 103,800×g for 90 minutes followed by suspension in 1 ml TBS (20 mM Tris, 500 mM NaCl at pH 7.5). The bacteriophage suspensions were layered over a 15 to 55% sucrose-TBS gradient and centrifuged at 103,800×g in a Beckman™ JS 24.38 rotor for 90 minutes. Bacteriophage bands were collected, concentrated by centrifugation, and the suspended pellets were placed on a 20% to 50% continuous potassium tartrate gradient (Misra et al., 1981) and centrifuged at 105,000×g in a Beckman™ JS 24.15 rotor for 90 minutes. The bacteriophage bands were drawn from the gradient, diluted in TBS and centrifuged at 105,000×g in a Beckman™ JS 24.15 rotor for 90 minutes followed by suspension in TBS. Purity of bacteriophages was examined by electron microscopy by methods known in the art. The bacteriophage pellets were subjected to proteinase K (20 mg/ml) digestion in the presence of 0.1% sarcosyl and 0.2 M EDTA followed by phenol-chloroform extraction (Sambrook et al., supra) to obtain genomic DNA by ethanol precipitation.

Example 2

The following example illustrates the molecular cloning, sequencing, annotation of genomic DNA and phylogenetic analyses.

Following purification of bacteriophage genomic DNA, the nucleic acid was subjected to spectrophotometer readings at 260/280 nm and restriction enzyme digestion followed by agarose gel electrophoresis to assess purity (Sambrook et al., supra). Full-length genome sequencing of the bacteriophage genomes was completed by MWG Biotech, Inc High Point, N.C. USA. Briefly, phage genomic DNA was sheared using a nebulizer, blunt-end repaired and dephosphorylated (Sambrook et al., 1989). DNA fragments of desired size (1 to 4 kb) were blunt-end ligated into pSmart (Lucigen™) for propagation in *E. coli* following transformation. Clones were sequenced such that approximately 14-fold redundancy was obtained for the genome that included primer-walking to fill gaps (Fouts et al., 2006). Molecular cloning was also completed using the restriction enzymes HindIII, EcoRI, EcoRV, AluI and ClaI to cleave phage genomic DNA followed by treatment with Taq polymerase (Lewis et al., 1992) and cloning (Mead et al., 1991) into the TOPO TA vector (Invitrogen™). Additionally, end-repair and G-tailing was completed for cloning restriction enzyme fragments into pSmart vectors (Lucigen™) for nucleotide sequencing. Double stranded nucleotide sequencing reactions using fluorescent labeled dideoxynucleotide terminators were completed and sequences determined using an automated sequencer (Smith et al., 1986; Applied Biosystems Inc.).

Nucleotide sequence editing, analysis, prediction of amino acid sequences and alignments were conducted using IntelliGenetics GeneWorks 2.5.1™ (IntelliGenetics, Mountain View, Calif.), MacVector 7.2™ (Accelrys, San Diego, Calif.) and DNASTAR™ (Madison, Wis.) software. Open reading frames (ORFs) in the final genome sequence were predicted using GeneMark.hmm for prokaryotes and ORF Finder software. The predicted protein amino acid sequences were searched against the protein database by using BLAST (Altschul et al., 1990) and PSI-BLAST or BLASTP (Altschul et al., 1997; Schäffer, 2001) as well as the conserved domain database (Marchler-Bauer, 2007) algorithms. Phylogenetic relationships among protein sequences were constructed with the Phylogenetic Analysis Using Parsimony (PAUP*4.0b; Swofford, 2001) software. All phylogenetic relationships generated were evaluated by 2000 bootstrap replicates (Hedges, 1992). The large terminase protein was utilized to predict the mechanism of DNA packaging and the structure of the virion ends (Casjens et al., 2005).

Example 3

The following example illustrates viron purification, two dimensional electrophoresis and proteomic analysis of isolated CP39O (PTA-11081) and CP26F (PTA-11080) bacteriophages.

Purified virion sample preparation for two dimensional (2D) gel electrophoresis. The bacteriophage protein purification was completed by adding four volumes of cold (−20° C.) acetone for at least one hour to the centrifuged phage pellet. The soluble protein fraction in acetone was centrifuged at 16,000×g for 10 minutes at 4° C. The pellet was washed in cold acetone/water (4:1) three times followed by centrifugation and dried under vacuum (Champion et al., 2001; Lee and Lee, 2003). To ensure reproducible gel electrophoresis purified virion protein fractions were digested with N-glycosidase F (PNGase F) to cleave oligosaccharides from N-linked glycoproteins (Maley et al., 1989) prior to extraction with acetone as per the manufacturer's instructions (New England BioLab™) for 1 hr at 37° C. Additionally, the water acetone pellets obtained following initial extraction were further purified following the procedure for "2-D gel clean-up" to remove interfering substances such as salts, detergents, lipids or phenolics (Amersham™)

Protein samples were suspended in electrophoresis buffer (5M urea, 2M thiourea, 2% CHAPS, 2% SB3-10, 0.2% 3/10 ampholyte with 40 mM Tris, pH 7.4). Samples were submitted to vortex followed by centrifugation at 16,000×g at 22° C. for 10 min. Proteomics analyses were completed by two-dimensional (2-D) gel electrophoresis (O'Farrell, 1975) as applied to bacteria (Champion et al. 2001; Lee and Lee, 2003). Proteins were suspended in lysate buffer followed by iso-electric focusing (pH 3-10) in the first dimension then by SDS-PAGE (O'Farrell, 1975; Bjellqvist et al., 1993). Spot detection and pattern matching was completed qualitatively on a Bio-Rad VersaDoc 4000 imager analyzing gels from each isolate in triplicate with PDQuest version 7.3.0 (Bio-Rad, Hercules, Calif.). Protein spots of interest were cored from 2-D gels and proteins extracted for peptide mass spectrometry fingerprinting. Spots were cut using BioRad EXQuest spot cutter and digested using Genomic Solutions Proprep (Finhout and Lee, 2003).

Identification of purified bacteriophage proteins by mass spectrometry. Tryptic peptide molecular masses obtained by MALDI-TOF-TOF MS (Aebersold et al., 1987; Lahm and Langen, 2000) were utilized to identify proteins by searching the protein sequence Mascot database at the National Center for Biotechnology Information, PIR and Swiss-Prot with ProFound (Proteomics, NY, N.Y.) and the predicted amino acid sequences from the bacteriophage genomes. Specifically, samples were prepared and spotted onto a MALDI (Matrix Assisted Laser Desorption Ionization) target using ZipTipu-C18 from Millipore. Samples were aspirated and dispensed with ZipTipu-C18 and eluted with conditioning solution (70% ACN, 0.2% formic acid) containing 5 mg/ml MALDI matrix (α-Cyano-4-hydroxycinnamic acid), 0.5 µl was spotted onto the MALDI target.

Samples were analyzed using Applied Biosystems 4700 Proteomics Analyzer with TOF/TOF Optics. MALDI-MS data was collected in the m/z range of 700 to 4000 using m/z of 842.51 and 2211.10 trypsin autolysis products as internal standards. Data was analyzed using Applied Biosystems GPS Explorer Software. All mass spectrometric data was collected using an ABI 4700 MALDI TOF/TOF (Applied Biosystems). The data was acquired in reflector mode from a mass range of 700-4000 Daltons and 1250 laser shots were averaged for each mass spectrum. Each sample was internally calibrated if both the 842.51 and 2211.10 ions from trypsin autolysis were present. If both ions were not found the instrument would use the default calibration. The eight most intense ions from the MS analysis not on the exclusion list were subjected to MS/MS. For MS/MS analysis the mass range was 70 to precursor ion with a precursor window of −1 to 3 Daltons with an average 5000 laser shots for each spectrum. The data was stored in an Oracle database.

The peptide data was extracted from the Oracle database and a peak list was created by GPS Explorer software (Applied Biosystems) from the raw data generated from the ABI 4700. This peak list was based on signal to noise filtering and an exclusion list and included de-isotoping. The resulting file was then searched by Mascot (Matrix Science). A tolerance of 20 ppm was used if the sample was internally calibrated and 200 ppm tolerance if the default calibration was applied. Protein identification was validated by the following criteria: greater than 20 ppm mass accuracy on all MS ions and all ions in at least two MS/MS spectra, which were not modified, had to be accounted for. Database search parameters include 1 missed cleavage, oxidation of methionines and carbamidomethylation of cysteines.

Example 4

The following Example illustrates PCR cloning of bacteriophage lysin genes. Amplification primers were designed to amplify the bacteriophage CP26F lysin and bacteriophage CP39O lysin genes while introducing restriction enzyme sites for sub-cloning into sequencing and expression vectors by methods known in the art (see e.g., Pritchard, D. G. et al. (2004) Microbiology 150:2079-2087.; Donovan, D. M. et al., (2006) Appl. Environ. Microbiol. 72:2988-96). For cloning the plyCP26F gene into pet21d, purified phiCP26F DNA was used as a template and amplified with primers plyCP26FexpF (5' TACCATGGT GAT AAT TGG AAG TAG ATA T 3'[SEQ ID NO:5]) and plyCP26F-plyCP39OexpR (5' GTG GTG CTCGAG TAT CTT TTC GGC AAA GCA AT 3'[SEQ ID NO:6]). The NcoI and XhoI restriction sites are underlined in the forward and reverse primers respectively. For cloning the plyCP39O gene into pet21a, purified phiCP39O DNA was used as a template and amplified with primers plyCP39OexpF (5' GCA CTA CATATG AAA ATA GCT TTA AGA GGT GGA 3'[SEQ ID NO:7]) and plyCP26F-plyCP39O expR (5' GTG GTG CTCGAG TAT CTT TTC GGC AAA GCA AT 3'[SEQ ID NO:8]). The NdeI and XhoI restriction sites are underlined in the forward and reverse primers respectively. PCR products were purified with spin-columns (Qiagen™) and digested with NcoI and XhoI (plyCP26F) or NdeI and XhoI (plyCP39O). The digested PCR products were spin-column purified and ligated with similarly digested vectors pet21d and pet21a, respectively. The resulting constructs were then transformed using E. coli Top 10 cells (Invitrogen™). Transformants were screened by digestion of isolated plasmids with the respective restriction enzymes nad by direct nucleotide sequencing. Plasmids containing the genes in the correct orientation for expression were then transformed into the E. coli Rosetta 2 (DE3) strains.

Thus, genes encoding the bacteriophage endolysins PlyCP39O and PlyCP26F were PCR amplified using the purified bacteriophage genomic DNAs as templates with oligonucleotide primers that included a Met start and the stop site to include a C-terminal His-tag.

The amplification products were cloned into sequencing and expression plasmids and transformed into E. coli. Since C. perfringens is a Gram positive organism, Rosetta strains were utilized for gene expression since, as known in the art, these bacteria also contain plasmids that provide appropriate tRNA genes to alleviate codon bias when expressing heterologous proteins in *E. coli* (see e.g., Kane, (1995) Curr. Opin. Biotechnol. 6:494-500). For the plyCP39O the Met start was intact while an ATG was incorporated into the plyCP26F start site primer since, the N-terminal amino acid in the original plyCP26F gene encoded a Val in the predicted protein.

Primary nucleotide sequencing of the cloned bacteriophage DNA confirmed the presence of both endolysin genes encoding proteins with predicted amino acid sequences for the respective bacteriophage endolysins. The genes were then expressed as C-terminal, His-tagged proteins and purified by Ni-column chromatography. The purified proteins were analyzed by gel electerophoresis that resulted in detection of two proteins each with a relative mobility corresponding to a molecular size of near 25,000. Both the *E. coli* lysates containing the expressed lysin and the purified proteins were capable of producing a clear "plaque" on a plate of confluent *C. perfringens* following a spot assay.

Example 5

The following Example illustrates the expression, extract preparation and protein purification of bacteriophage lysins.

*Escherichia coli* Rosetta 2 (DE3) cells harboring plasmid constructs described above in Example 4, were propagated in 200 ml Lurea Bertani (LB) broth supplemented with 100 μg/ml ampicillin and 34 μg/ml chloramphenicol at 37 C with shaking. Mid log phase ($OD_{600nm}$ of 0.4 to 0.6) cultures were placed on ice for 30 minutes, followed by induction with 1 mM isopropyl-beta-D-thiogalactopyranoside (IPTG), and then incubated at 20 C for 18 hours with shaking. Cultures were centrifuged at 5000×g for 20 minutes at 4 C. Cell pellets were frozen at −80° C. Pellets were allowed to thaw on ice and suspended in 4 ml of lysis buffer (50 mM $NaH_2PO_4$, 300 mM NaCl, 10 mM imidazole, 10% glycerol, pH 8). The suspension was then sonicated (15×5 second pulses with 15 seconds rest on ice between pulses) and centrifuged for 30 minutes at 5000×g at 4 C. The resulting supernatant was used as clarified lysate. One ml of Ni-NTA (nickel matrix) slurry was added to the clarified lysate according to the manufacturers instructions (Qiagen, Valencia, Calif.) with gentle shaking for 1 hour at 4 C. The slurry was then applied to the column and allowed to flow through by gravity. The column was washed twice with 4 ml of wash buffer (50 mM NaH2PO4, 300 mM NaCl, 20 mM imidazole, 10% glycerol at pH 8.0) and eluted with 2 ml sample buffer (50 mM NaH2PO4, 300 mM NaCl, 250 mM imidazole, 10% glycerol at pH 8.0).

Example 6

The following Example illustrates biochemical characterizations of bacteriophage lysin proteins.

Protein concentrations in samples prepared as described above in Example 5, were determined using the Qubit flouremeter (Invitrogen, Carlsbad, Calif.). Eluted proteins and Kaleidoscope™ protein standards (Invitrogen, Carlsbad, Calif.) were analyzed with 4-20% precise protein gels (Pierce, Rockford, Ill.) run in Tris-Hepes-SDS buffer at 120V for 1 hour in the BioRad Mini-PROTEAN three gel apparatus, according to the manufacturer's instructions (see e.g., Hames, B. D. (1981) An introduction to polyacrylamide gel electrophoresis. In: B. D. Hames and D. Rickwood (Eds), *Gel Electrophoresis of Proteins: A Practical Approach*, IRL Press, Oxford. pp. 1-91). Gels were stained with Coomassie Brilliant Blue R-250 (BioRad, Hercules, Calif.) for 1 h, washed overnight in distilled water and photographed.

Purified recombinant bacteriophage lysins were amino acid sequenced directly by Edman degradation. The sample was applied to PVDF by filtration through a ProSorb device (ABI). Sequencing was performed using standard pulse liquid cycles on an ABI Procise 492 HT sequencer by methods known in the art (see e.g., Niall, H. D. (1973) Meth. Enzymol. 27: 942-1010). Additionally protein sequences were determined by mass spectrometry analyses with some modifications as known in the art (see e.g., Hunt et al., (1986) Proc. Natl. Acad. Sci. USA. 83:6233-7; Rosenfeld, J. et al., (1992) Anal. Biochem. 203: 173-179). All mass spectrometric data were collected using an ABI 4700 Proteomics Analyzer MALDI TOF/TOF mass spectrometer (Applied Biosystems, CA), using the 4000 Series Explorer software v. 3.6. The data was extracted from the Oracle database and a peak list was created by GPS Explorer software v 3.6 (Applied Bio systems) from the raw data generated from the ABI 4700. Analyses were performed as combination MS+MS/MS.

The single bands from SDS-PAGE were extracted and subjected to N-terminal amino acid sequence and analysis by mass spectrometry as discussed above. Both techniques confirmed that the primary amino acid sequences of the proteins were as predicted from the nucleotide sequence of each cloned gene. BLAST analyses of the bacteriophage lysins resulted in each of the proteins predicted to be an N-acetylmuramoyl-L-alanine amidase or MurNAc-LAA (also known as peptidoglycan aminohydrolase, NAMLA amidase, NAMLAA, amidase 3, and peptidoglycan amidase; EC 3.5.1.28) which are autolysins that hydrolyze the amide bond between N-acetylmuramoyl and L-amino acids in bacterial cell wall glycopeptides (see e.g., Vollmer et al. (2008) FEMS Microbiol Rev. 32:259-86).

The lysin genes were cloned from two bacteriophages that have host ranges restricted to individual isolates of *C. perfringens*. Overall the genomes of these two bacteriophages shared greater than 95% sequence similarity. As noted earlier, despite the high overall sequence similarity between the two genomes the lysins' predicted protein amino acid sequences were identical at the C-terminus cell-wall binding domain, but were only 55 percent similar to each other at the N-terminal catalytic domain (FIG. 5). In particular, residues 164 through 213 of PlyCP39O were identical to residues 163 through 212 of PlyCP26F. The variable N-terminal residues of the proteins to position 162 were both predicted as N-acetylmuramoyl-L-alanine amidases. Furthermore, the PlyCP39O and PlyCP26F were more closely related to the published bacteriophage amidase-type lysins reported from *C. difficile* rather than from *C. perfringens*. However, amidase-type lysins from *C. difficile* are not expected to lyse *Clostridium perfringens* bacteria since the cell wall binding domain of the proteins, which accounts for species specificity, differs in *C. difficile* and *C. perfringens*.

Although BLAST analyses revealed the presence of closely related predicted proteins encoded in the genomes of a variety of other Gram-positive bacteria Example 7

The following Example illustrates testing the ability of isolated *Clostridium perfringens* bacteriophage lysin activity using spot and turbidity assays.

Purified recombinant protein or the *E. coli* lysate expressing the bacteriophage lysins were used to determine the ability of the isolated lysins to lyse *C. perfringens* on bacterial plates using methods known in the art (see e.g., Zimmer et al., 2002; Donovan et al., (2006) supra). The reduction in turbidity as a result of target cell lysis due to the activity of phage derived lysin was measured by monitoring the change in optical density ($OD_{600nm}$) over time (Zimmer et al., 2002; Donovan et al., 2006). Target cells were grown to mid log phase ($OD_{600nm}$ 0.4-0.6) in Brain Heart Infusion (BHI) broth (Becton Dickenson, Franklin Lakes, N.J.) and concentrated in lysine buffer A (LBA 50 mM ammonium acetate, 10 mM $CaCl_2$, 1 mM DTT, pH 6.2) to an $OD_{600nm}$~1.0. Assays were completed in 96-well microtiter plates with 344 μl of target cell suspension in each well and 10 μl of purified peptide (~2.5 μg) for treated samples and 10 μl of buffer for control samples. Change in $OD_{600nm}$ was recorded after 1 hour incubation at 37 C. Changes in the cell samples alone were subtracted from samples with lysin, before calculating the activity (change in $OD_{600nm}$ mg $protein^{-1}$ $min^{-1}$).

Effect of pH on bacteriophage derived lysin activity. Activity of phage derived lysins in response to pH was measured as described in the turbidity assay method but with the pH of LBA adjusted using either glacial acetic acid or ammonium hydroxide (Yoong et al., 2004). The pH with the highest activity was arbitrarily set at 100% and the activity at other pH values were expressed relative to this optimal activity.

Turbidity assays and pH range of recombinant lysins. Both recombinant lytic enzymes were used to measure lysis of *C. perfringens* in turbidity assays (FIG. 2). The recombinant bacteriophage lytic enzymes were capable of lysing both parental bacteriophage host strains of *C. perfringens* as well as thirteen other isolates of the bacterium in turbidity reduction assays. That is PlyCP39O was capable of lysing host Cp39 which was deposited on Aug. 13, 2010 with the American Type Culture Collection (ATCC) under the provisions of the Budapest Treaty and assigned the Deposit Designation PTA-11265 and host Cp26 which was deposited on Aug. 13, 2010 with the American Type Culture Collection (ATCC) under the provisions of the Budapest Treaty and assigned the Deposit Designation PTA-11264 while PlyCP26F could reduce turbidity if utilizing isolates Cp26 or Cp39. This was despite the fact that the predicted N-terminal enzymatic regions differed by 55% in their amino acid sequences. The reduction in turbidity was accompanied by up to a 3 log cfu/ml reduction in viable *C. perfringens* on BHI (brain heart infusion) agar plates following a one-hour incubation period. Although all *C. perfringens* isolates assayed underwent lysis neither one of the enzymes were capable of lysing other members of the clostridia. The optimal pH range varied from 5.5 to 9.9 for PlyCP26F while the pH maximum was 8.2 for PlyCP39O.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An isolated *Clostridium perfringens* bacteriophage lytic enzyme, wherein the bacteriophage lytic enzyme is CP26F lysin and wherein, the isolated *Clostridium perfringens* bacteriophage lytic enzyme is expressed in an expression vector as a recombinant protein comprising an amino acid sequence that is at least about 90% identical to SEQ ID NO: 1 and a carboxy-terminal His-Tag, and wherein the bacteriophage lytic enzyme has activity that results in lysis of *Clostridium perfringens* bacterial cells.

2. The isolated *Clostridium perfringens* bacteriophage lytic enzyme of claim 1, wherein the bacteriophage lytic enzyme comprises an amino acid sequence that is at least about 95% identical to SEQ ID NO: 1.

3. The isolated *Clostridium perfringens* bacteriophage lytic enzyme of claim 1, wherein the bacteriophage lytic enzyme comprises an amino acid sequence that is at least about 98% identical to SEQ ID NO: 1.

4. The isolated *Clostridium perfringens* bacteriophage lytic enzyme of claim 1, wherein the bacteriophage lytic enzyme comprises an amino acid sequence that is at least about 99% identical to SEQ ID NO: 1.

5. The isolated *Clostridium perfringens* bacteriophage lytic enzyme of claim 1, wherein the bacteriophage lytic enzyme is SEQ ID NO: 1.

6. The isolated *Clostridium perfringens* bacteriophage lytic enzyme of claim 1, wherein the bacteriophage lytic enzyme isolated from *Clostridium perfringens* Bacteriophage CP26F having an ATCC deposit designation PTA-11080.

7. The isolated *Clostridium perfringens* bacteriophage lytic enzyme of claim 1, wherein the bacteriophage lytic enzyme is a member selected from the group consisting of peptide comprising an amino acid sequence identical to amino acids 1-158 of SEQ ID NO: 1; and peptide comprising an amino acid sequence identical to amino acids 1-212 of SEQ ID NO:1.

8. An antimicrobial composition effective against *Clostridium perfringens* comprising a *Clostridium perfringens* bacteriophage lytic enzyme, wherein, the bacteriophage lytic enzyme is a CP26F lysin and wherein, the isolated *Clostridium perfringens* bacteriophage lytic enzyme is expressed in an expression vector as a recombinant protein comprising an amino acid sequence that is at least about 90% identical to SEQ ID NO: 1 and a carboxy-terminal His-Tag, and wherein the bacteriophage lytic enzyme has activity that results in lysis of *Clostridium perfringens* bacterial cells.

9. The antimicrobial composition of claim 8, wherein the bacteriophage lytic enzyme is SEQ ID NO:1.

10. The antimicrobial composition of claim 8, wherein the bacteriophage lytic enzyme expressed from in an expression vector as a recombinant protein is expressed from a nucleic acid isolated from *Clostridium perfringens* Bacteriophage CP26F having an ATCC deposit designation PTA-11080.

11. The antimicrobial composition of claim 8, wherein the bacteriophage lytic enzyme is a member selected from the group consisting of peptide comprising an amino acid sequence identical to amino acids 1-158 of SEQ ID NO: 1; and a peptide identical to amino acids 1-212 of SEQ ID NO:1.

12. An animal feed comprising a *Clostridium perfringens* bacteriophage lytic enzyme, wherein the bacteriophage lytic enzyme is a CP26F lysin, and wherein, the isolated *Clostridium perfringens* bacteriophage lytic enzyme is expressed in an expression vector as a recombinant protein comprising an amino acid sequence that is at least about 90% identical to SEQ ID NO: 1 and a carboxy-terminal His-Tag, and wherein the bacteriophage lytic enzyme is present in an amount effective for controlling *Clostridium perfringens* infection in livestock.

13. The animal feed of claim 12, wherein the livestock is chickens.

14. The animal feed of claim 12, wherein the *Clostridium perfringens* bacteriophage lytic enzyme has an amino acid sequence identical to SEQ ID NO: 1.

15. The animal feed of claim 12, wherein the *Clostridium perfringens* bacteriophage lytic enzyme is a member selected from the group consisting of peptide comprising an amino acid sequence identical to amino acids 1-158 of SEQ ID NO: 1; and peptide comprising an amino acid sequence identical to amino acids 1-212 of SEQ ID NO:1.

16. An isolated *Clostridium perfringens* bacteriophage lytic enzyme, wherein the bacteriophage lytic enzyme is expressed in an expression vector as a recombinant protein consisting of amino acids 1-158 of SEQ ID NO:3 and a carboxy-terminal His-Tag, and wherein the bacteriophage lytic enzyme has activity that results in lysis of *Clostridium perfringens* bacterial cells.

17. An animal feed comprising a *Clostridium perfringens* bacteriophage lytic enzyme of claim 16 and wherein the bacteriophage lytic enzyme is present in an amount effective for controlling *Clostridium perfringens* infection in livestock.

* * * * *